(12) United States Patent
Gupta et al.

(10) Patent No.: US 11,524,095 B2
(45) Date of Patent: Dec. 13, 2022

(54) MEDICAL DELIVERY DEVICES AND METHODS OF MAKING AND USING SAME

(71) Applicant: St. Jude Medical, Cardiology Division, Inc., St. Paul, MN (US)

(72) Inventors: Pankaj Gupta, Maple Grove, MN (US); Matt Glimsdale, St. Michael, MN (US); Michael Meyer, Minnetrista, MN (US); Kevin Dunne, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 616 days.

(21) Appl. No.: 16/314,230

(22) PCT Filed: Jun. 28, 2017

(86) PCT No.: PCT/US2017/039687
§ 371 (c)(1),
(2) Date: Dec. 28, 2018

(87) PCT Pub. No.: WO2018/005614
PCT Pub. Date: Jan. 4, 2018

(65) Prior Publication Data
US 2019/0224383 A1 Jul. 25, 2019

Related U.S. Application Data

(60) Provisional application No. 62/356,757, filed on Jun. 30, 2016.

(51) Int. Cl.
*A61M 25/00* (2006.01)
*A61L 29/08* (2006.01)
(Continued)

(52) U.S. Cl.
CPC .......... *A61L 29/085* (2013.01); *A61L 29/146* (2013.01); *C09D 127/06* (2013.01);
(Continued)

(58) Field of Classification Search
CPC .. A61L 29/085; A61L 29/146; A61L 2420/02; A61M 25/0045; A61M 2025/0047; C09D 127/06
See application file for complete search history.

(56) References Cited

U.S. PATENT DOCUMENTS

| | | | | |
|---|---|---|---|---|
| 2,472,484 A | * | 6/1949 | Krippendorf | ..... A61M 25/0054 604/525 |
| 4,817,613 A | * | 4/1989 | Jaraczewski | ...... A61M 25/0012 138/125 |

(Continued)

OTHER PUBLICATIONS

International Search Report and Written Opinion issued in PCT/US2017/039687, dated Dec. 5, 2017, 15 pages.

*Primary Examiner* — Kelly J Bekker
*Assistant Examiner* — Andrew P. Restaino
(74) *Attorney, Agent, or Firm* — Armstrong Teasdale LLP

(57) ABSTRACT

The present disclosure provides improved medical delivery devices for delivering a medical device into a subject. In one embodiment, the medical delivery device includes a nonporous composite inner layer constructed of a lubricious material having a plurality of pores and a thermoplastic elastomer reflowed into the plurality of pores. In other embodiments, the medical delivery device further includes a thermoplastic elastomer coated braided metallic member surrounding the nonporous composite inner layer to provide strength and structure to the device.

4 Claims, 9 Drawing Sheets

(51) Int. Cl.
*A61L 29/14* (2006.01)
*C09D 127/06* (2006.01)

(52) U.S. Cl.
CPC ...... *A61L 2420/02* (2013.01); *A61M 25/0045* (2013.01); *A61M 2025/0047* (2013.01)

(56) References Cited

U.S. PATENT DOCUMENTS

| | | | | |
|---|---|---|---|---|
| 5,868,704 | A * | 2/1999 | Campbell | C08L 75/04 604/103.11 |
| 6,902,571 | B2 * | 6/2005 | Owens | A61M 25/104 604/103.06 |
| 2002/0173815 | A1 * | 11/2002 | Hogendijk | A61F 2/013 606/194 |
| 2004/0197501 | A1 | 10/2004 | Sridharan | |
| 2005/0283221 | A1 * | 12/2005 | Mann | A61M 25/0054 623/1.11 |
| 2008/0317991 | A1 * | 12/2008 | Pieslak | A61L 29/041 428/36.91 |
| 2010/0206453 | A1 * | 8/2010 | Leeflang | A61M 25/005 156/60 |
| 2012/0059448 | A1 * | 3/2012 | Parker | A61F 2/966 623/1.11 |
| 2015/0320971 | A1 * | 11/2015 | Leeflang | C08J 7/056 604/527 |
| 2016/0067444 | A1 * | 3/2016 | Allen | A61M 25/007 604/246 |

\* cited by examiner

MEDICAL DELIVERY DEVICES AND METHODS OF MAKING AND USING SAME

CROSS-REFERENCE TO RELATED APPLICATIONS

This application is the national stage entry of PCT/US2017/039687, filed on Jun. 28, 2017, which claims the benefit of U.S. Provisional Patent Application No. 62/356,757, filed Jun. 30, 2016, the contents of which are hereby incorporated by reference herein in their entirety.

BACKGROUND OF THE DISCLOSURE a. Field of the Disclosure

The present disclosure generally relates to medical delivery devices and methods of making and using the same. In particular, the present disclosure relates to medical delivery sheaths and delivery catheters that include a durable and lubricious composite inner layer and methods of making and using these medical delivery sheaths and catheters.

b. Background Art

A variety of medical devices are used in medical procedures. Certain intravascular delivery devices, such as delivery catheters and sheaths, are generally used to deliver, or guide, medical devices or instruments to a target location within a subject. The delivery devices provide access to target locations within the body where, for example, diagnostic, therapeutic, and interventional procedures are required. Access via these devices is generally minimally invasive, and can be either percutaneous, or through natural body orifices. The access can require providing a guiding path through a body lumen, such as, for example a blood vessel. Once the delivery device has provided access to the target location, the delivery device is then used to guide the medical device or instrument to perform the diagnostic, therapeutic, or interventional procedure. An example of such a delivery device is a guide catheter, which may be delivered by steering it to its required destination, tracking it along a previously delivered guide wire, or both.

SUMMARY OF THE DISCLOSURE

The present disclosure is directed to a medical delivery device for introducing a medical device into a subject. The medical delivery device comprises a substantially non-porous composite liner comprising a lubricious material having a plurality of pores and a first reflowed thermoplastic elastomer substantially filling the plurality of pores.

The present disclosure is further directed to a medical delivery device for introducing a medical device into a subject. The medical delivery device comprises a lubricious material having a plurality of pores surrounded by a metallic material having a plurality of pores and a reflowed thermoplastic elastomer substantially filling the plurality of lubricious material pores and metallic material pores.

The present disclosure is further directed to a medical delivery device for introducing a medical device into a subject. The medical delivery device comprises a metallic substrate coated with a lubricious material. The coated metallic substrate is configured to comprise a plurality of pores. The medical delivery device further comprises a reflowed thermoplastic elastomer substantially filling the plurality of pores.

The present disclosure is further directed to a method of making a medical delivery device. The method comprises (i) reflowing a first thermoplastic elastomer over a lubricious material having a plurality of pores to substantially fill the plurality of pores and provide a composite liner; (ii) surrounding the composite liner with a metallic material having a plurality of pores; and (iii) reflowing a second thermoplastic elastomer over the metallic material to substantially fill the plurality of pores on the metallic material.

The present disclosure is further directed to a method of making a medical delivery device. The method comprises (i) surrounding a lubricious material having a first plurality of pores with a metallic material having a second plurality of pores; and (ii) reflowing a thermoplastic elastomer over the lubricious material and metallic material to substantially fill in the first plurality of pores and the second plurality of pores.

The present disclosure is further directed to a method of making a medical delivery device. The method comprises (i) coating a metallic substrate with a lubricous material; (ii) forming a structure having a plurality of pores from the coated metallic substrate; and (iii) reflowing a thermoplastic elastomer over the structure to substantially fill in the plurality of pores in the structure.

DETAILED DESCRIPTION OF THE DISCLOSURE

Figure 1:
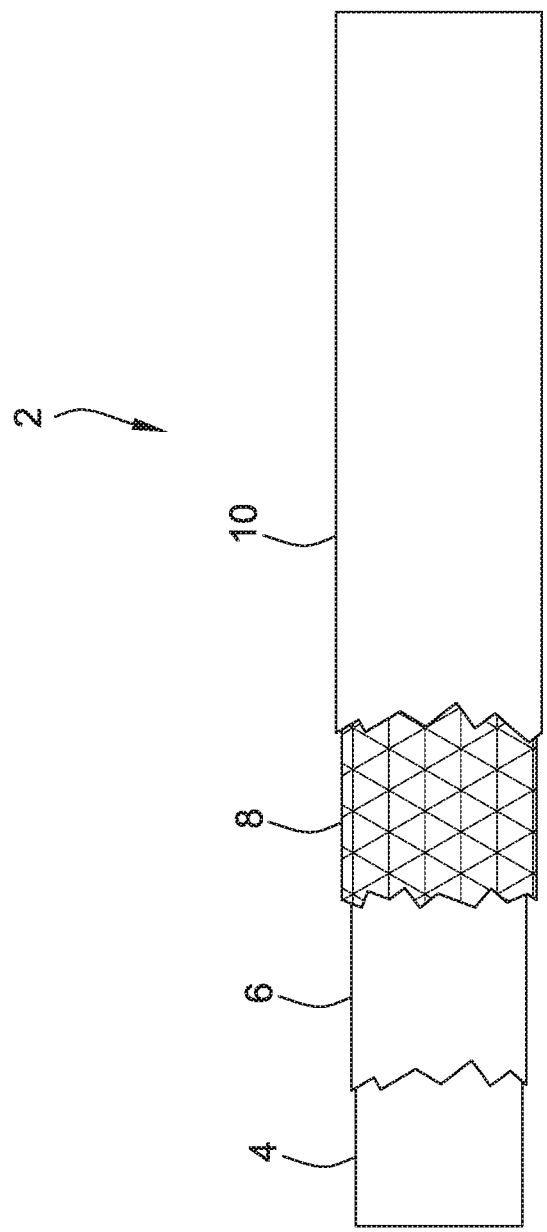
FIG. 1 shows a cut-away view of conventional medical delivery device.

Many medical delivery devices are constructed of multiple layers to provide a combination of user benefits including, for example, strength, durability, flexibility, and a smooth, low friction, inner surface for a medical device to travel along. Because some medical devices may be recaptured into the medical delivery device during a medical procedure for a variety of reasons, it is generally desirable that the innermost layer of the delivery device provide a lubricious and durable surface capable of allowing both passage and recapture of the medical device.

Thus, it is desirable to provide a medical delivery device that includes an inner-most layer or surface that is both lubricious and durable such that the medical device being delivered can smoothly pass through the medical delivery device and into the body without damage to the medical device or the medical delivery device. It is also desirable to provide methods of making and using such medical delivery devices. The present disclosure is directed to medical delivery devices, and methods of making and using the medical delivery devices, that provide an inner-most layer or surface that is highly lubricious and durable such that medical devices and be easily and safely delivered and/or recaptured as needed without damage to either the medical device or the delivery device.

The medical delivery devices described herein are designed for use with a wide variety of medical devices and implants, including medical devices and implants that include one or more stabilizing wires on the circumference thereof. In one embodiment of the present disclosure, the medical delivery device includes a substantially non-porous composite liner layer as the inner-most layer of the medical delivery device. This substantially non-porous composite liner layer comprises at least a combination of a lubricious material including a plurality of pores or openings and a reflowed thermoplastic elastomer that substantially fills in the pores to provide a composite material providing multiple benefits to the medical delivery device. The lubricous material provides this inner-most layer of the medical delivery device with desirable low-friction properties while the thermoplastic elastomer provides substantial durability and strength. In another embodiment, the non-porous composite layer further includes a metallic material having a plurality of pores that surrounds the composite layer. In many embodiments, a thermoplastic elastomer is reflowed on the metallic layer having a plurality of pores so as to substantially fill the plurality of pores. In yet another embodiment, the inner-most surface of the medical delivery device comprises a woven metallic substrate coated with a lubricious material. The coated woven metallic substrate forms a plurality of pores that are substantially filled in with a reflowed thermoplastic elastomer.

In many embodiments the thermoplastic elastomers described herein are melted and reflowed into the pores of the lubricous material (or pores created by a braided or wound substrate) and the pores of the metallic material to provide long-lasting, low-friction and durable medical delivery devices capable of safely and effectively delivering and recapturing medical devices. It has been unexpectedly found that that a lubricious material having a plurality of pores, such as a polytetrafluoroethylene material having a plurality of pores, can have a thermoplastic elastomer, such as a polyether block amide, reflowed thereon and into the pores present in the lubricious material such that the resulting composite material retains the high lubricity benefit of the polytetrafluoroethylene material and the durability benefit of the thermoplastic elastomer. Since the lubricious material includes a plurality of pores and is not provided as a continuous layer, this allows both the lubricious material and the reflowed thermoplastic elastomer to be present on the inner surface of the device, the resulting composite material includes beneficial attributes from both the lubricous material and the reflowed thermoplastic elastomer. The resulting composite material may be used as the inner-most layer of a medical delivery device to provide easy pass-through of a medical device, as well as high strength and durability. Subsequent layers of porous metallic materials and thermoplastic elastomers may also be used to improve the functionality, flexibility, and strength of the medical delivery device. Other embodiments are also provided herein.

Referring now to FIG. 1, there is shown a conventional medical delivery device 2. Medical delivery device 2 is constructed of multiple layers and includes inner layer 4 surrounded by a first thermoplastic elastomer layer 6 surrounded by metallic layer 8 surrounded by second thermoplastic elastomer layer 10. Inner layer 4 is the innermost layer of medical delivery device 2 and is the layer that contacts a medical device during delivery. Inner layer 4 has conventionally been constructed of a non-porous low friction material such as a polytetrafluoroethylene material to facilitate movement of a medical device through the delivery device. First and second thermoplastic elastomer layers 6 and 10 are generally constructed of a thermoplastic elastomer to provide strength and a smooth outer surface. Metallic layer 8, which is generally constructed of a stainless steel or equivalent material, provides strength and flexibility to the medical delivery device. Because some medical devices may be recaptured into medical delivery device 2 during a medical procedure for a variety of reasons, it is generally desirable that the innermost layer of the delivery device provide a lubricious and durable surface capable of allowing both passage and recapture of the medical device.

Figure 2:
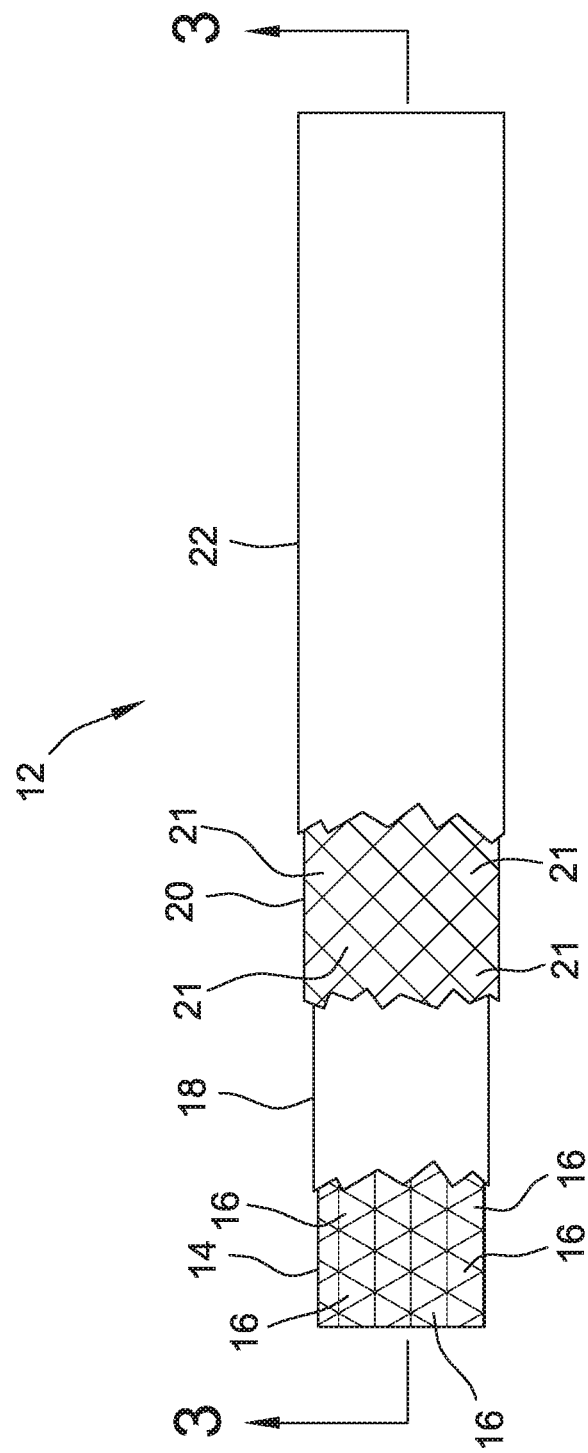
FIG. 2 shows a cut-away view of one embodiment of a medical delivery device of the present disclosure.

Referring now to FIG. 2, there is shown a cut away view of one embodiment of a medical delivery device 12 of the present disclosure to show the various layers of medical delivery device 12 including an inner layer 14 having a plurality of pores 16. As used herein, the term "porous" refers to a material that is permeable to air and/or water and includes pores. As used herein, the term "pores" refers to holes, openings, and/or channels in a material or structure (i.e., a braided structure, a wound or coiled structure, etc.) through which air or water may pass. In the context of the current disclosure, it is the reflowed thermoplastic elastomer (as described in more detail below) that passes into the pores in the lubricious material such that it may be exposed on both an outer surface and an inner surface of the lubricious material. Referring again to FIG. 2, medical delivery device 12 includes inner layer 14 comprised of a lubricious material and having a plurality of pores 16. Inner layer 14 is surrounded and intermixed (see FIG. 3 discussed below) with first thermoplastic elastomer layer 18, which is surrounded by metallic layer 20 having a plurality of pores 21, which is surrounded and intermixed (see FIG. 3 discussed below) with second thermoplastic elastomer layer 22.

Figure 3:
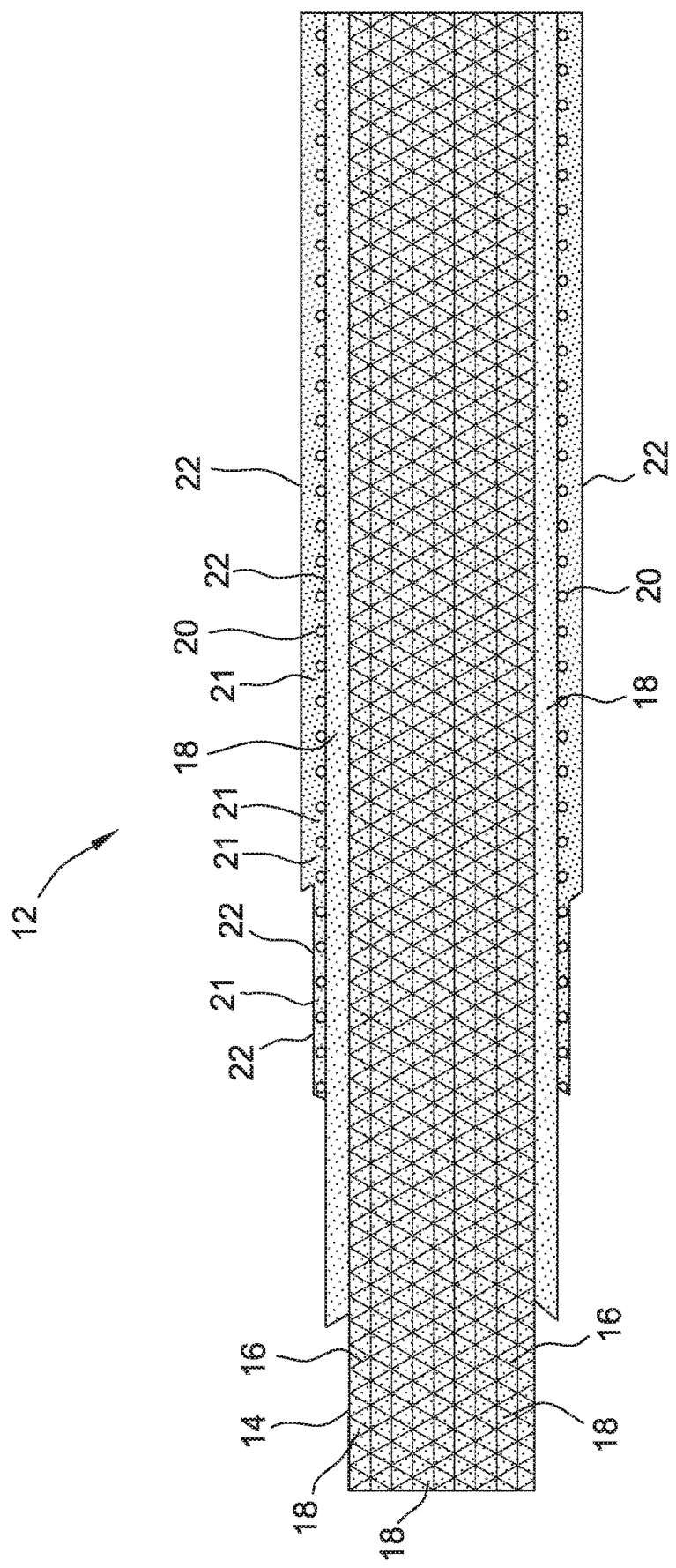
FIG. 3 shows a longitudinal cross-section taken along 3-3 of the medical delivery device of FIG. 2.

Referring now to FIG. 3, there is shown a cross-sectional view of medical delivery device 12 of FIG. 2 taken along line 3-3 to show additional details about the various layers, and specifically inner layer 14. FIG. 3 shows inner layer 14 including first thermoplastic elastomer 18 present in plurality of pores 16 of inner layer 14 such that a non-porous composite inner layer including both lubricious material and thermoplastic elastomer is formed. As such, inner layer 14 becomes non-porous in nature. Because inner layer 14 includes plurality of pores 16, during manufacturing when first thermoplastic elastomer 18 is reflowed over inner layer 14 (as described in greater detail below), first thermoplastic elastomer 18 flows into plurality of pores 16 to create a composite material having attributes from both the inner layer 14 (lubricious, low friction attributes) and first thermoplastic elastomer 18 (durability and strength attributes). Further, FIG. 3 shows metallic layer 20 including second thermoplastic elastomer 22 present in plurality of pores 21 of metallic layer 20. This combination of two thermoplastic elastomers (18 and 22) provides a medical delivery device 12 with a strong and durable composite inner layer and a strong, smooth outer surface.

The lubricious material including the plurality of pores as described herein that forms part of the inner layer of the medical delivery device may be manufactured from any material that provides the desired low friction properties and lubricous nature. For example, the lubricious material may be polytetrafluoroethylene (PTFE) including expanded PTFE (ePTFE), fluorinated ethylene propylene (FEP) including expanded FEP (eFEP), polyethylene terephthalate (PET), and the like, and combinations thereof. In some embodiments, PTFE is a desirable lubricous material.

The lubricous material may be utilized in the medical delivery devices of the present disclosure in any number of forms so as to provide the desired plurality of pores to be substantially filled in with the reflowed thermoplastic elastomer as described herein. For example, the lubricious material may be in the form of a mesh-like material having holes (laser drilled holes, for example) to create the pores in the material. In some embodiments, the lubricious material may be in the form of a tubular mesh material while in other embodiments the lubricious material may be in the form of a planar material created from a desired monofilament fiber. As will be recognized by one skilled in the art based on the disclosure herein, the overall lubricity and durability of the lubricious material (and thermoplastic elastomer present in the pores as described herein) provided to the resulting medical delivery device can be varied and controlled by varying the spacing (i.e., varying the size and/or density of the pores) in the mesh material so as to control the relative surface area of each component. In some embodiments, the mesh material may have a suitable thickness of from about 0.001 inches to about 0.005 inches, including from about 0.002 inches to about 0.0015 inches. In some embodiments, the surface area may comprise from about 50% to about 90% lubricious material, with the remainder being the thermoplastic polymer.

Other examples of the form of the lubricious material in the medical delivery devices include a braided form created by braiding a lubricious material monofilament (such as a PTFE monofilament) onto a mandrel to form a tubular braid and winding a lubricious material monofilament onto a mandrel to form a wound coil. The braided material and wound coil material will include a plurality of monofilament strands having a predetermined relative orientation between the strands that provides the desired pores. As will be recognized by one skilled in the art based on the disclosure herein, a number of factors such as thickness or diameter of the monofilament, pitch of the monofilament strands, pick of the fabric etc. may be controlled and adjusted to impact the overall lubricity and durability of the lubricious material (and thermoplastic elastomer present in the pores as described herein) provided to the resulting medical delivery device. In some embodiments, the braid density may be from about 25 to about 100 PPI. In other embodiments, the coil may include right or left-handed coils having a pitch of from about 1.25 times to about 3 times that of the monofilament wire diameter.

In many embodiments described herein, the monofilament lubricious material (such as a PTFE monofilament material) fibers are in the form of a mesh, braid or coil as noted above. In these forms, the monofilament lubricious material fibers are generally oriented at an angle with respect to the axis of the overall medical delivery device being manufactured. Because these monofilament lubricious material fibers are not oriented parallel to the access of the medical delivery device, deployment and recapture of a medical device may be improved. Additionally, the PTFE liners are more robust and more durable as the thermoplastic material encapsulates the lubricious material on all sides thereof.

The thermoplastic elastomers as described herein that are melted and reflowed (otherwise applied) and allowed to cure so as to form the thermoplastic elastomer layer(s) of the medical delivery device may be any material that provides the desired durability and strength properties while allowing for a specific stiffness and bend strength. Suitable examples include polystyrene, polyvinyl chloride, ethylene vinyl acetate, polyether block amide, polyamide, thermoplastic polyurethane, and combinations thereof. Other suitable heat settable plastics or superplastics are known to those or ordinary skill in the art. In some embodiments, particularly desirable thermoplastic elastomers include PEBAX® (Arkema, Colombes, France) polyether block amides. The thermoplastic elastomers utilized in the medical delivery devices of the present disclosure have a durometer value suitable for their intended purpose; that is, they have a durometer value suitable to impart durability, strength, and flexibility to the resulting medical delivery devices. In some embodiments, a durometer value of from about 20 D to about 100 D, including from about 50 D to about 80 D may be desirable. When two or more thermoplastic elastomers are present in a medical delivery device of the present disclosure, the thermoplastic elastomers may be the same or different thermoplastic elastomers, which may have the same or different durometer values. In some embodiments, the thermoplastic elastomer may have a thickness of from about 0.001 inches to about 0.005 inches, and may be cured as desired at a temperature of from about 180° C. to about 250° C. for a time period of from about 1 minute to about 10 minutes.

The metallic layer that surrounds at least the lubricous material having a plurality of pores as described herein may be constructed of any suitable material the provides the desired combination of strength and flexibility. Such materials are known to one skilled in the art and include, for example, stainless steel, nitinol, other metallic alloys, and the like. In many embodiments, the metallic layer will include a braided metallic material that may be in the form of a braided tubular material. In other embodiments, the metallic layer will include a wound coil metallic material. In other embodiments, the metallic layer will include a Helical Hollow Strand™ (HHS). In some desirable embodiments the metallic layer will include a braided stainless steel tubular material. In some embodiments, the diameter of the metallic wire may be from about 0.001 inches to about 0.005 inches.

Figure 4:
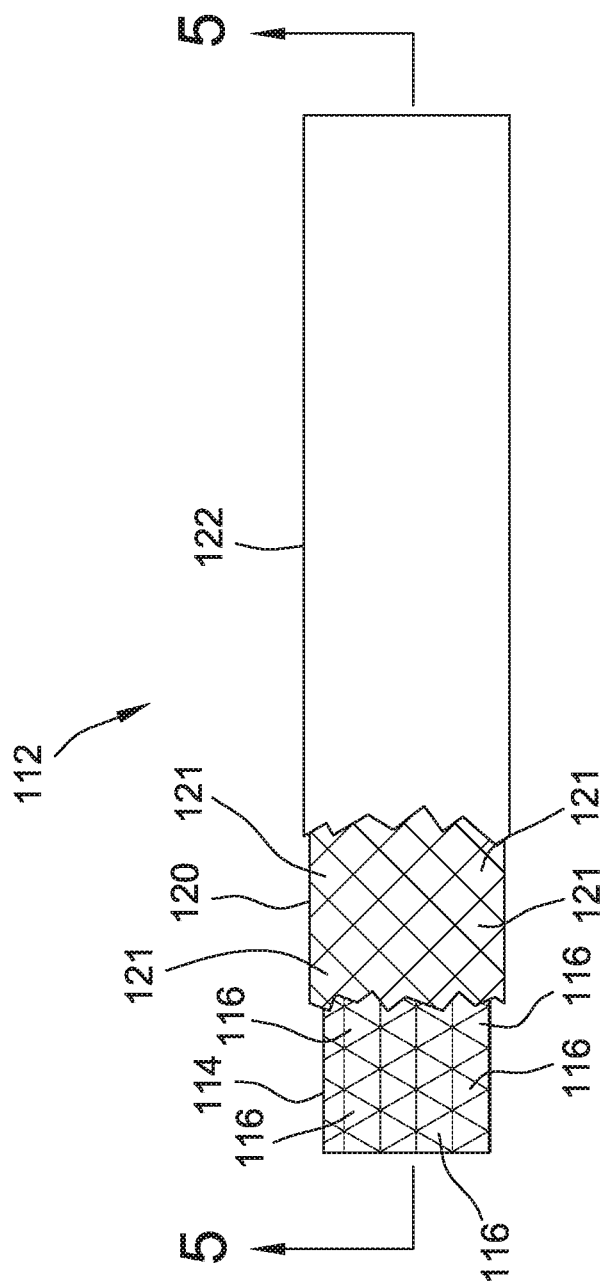
FIG. 4 shows a cut-away view of another embodiment of a medical delivery device of the present disclosure.

In another embodiment of the present disclosure, the medical delivery device includes only a single layer of a reflowed thermoplastic elastomer. In this embodiment, the single layer of reflowed thermoplastic elastomer contacts and intermixes with both a lubricous material having a plurality of pores and metallic layer having a plurality of pores. Referring now to FIG. 4, there is shown a cut away view of one embodiment of a medical delivery device 112 of the present disclosure to show the various layers of medical delivery device 112 including an inner layer 114 comprised of a lubricious material and having a plurality of pores 116. Inner layer 114 is surrounded by metallic layer 120 having a plurality of pores 121. Inner layer 114 and metallic layer 120 are intermixed (see FIG. 5 discussed below) with thermoplastic elastomer layer 122 to form a medical delivery device 112 that includes a single thermoplastic elastomer.

Figure 5:
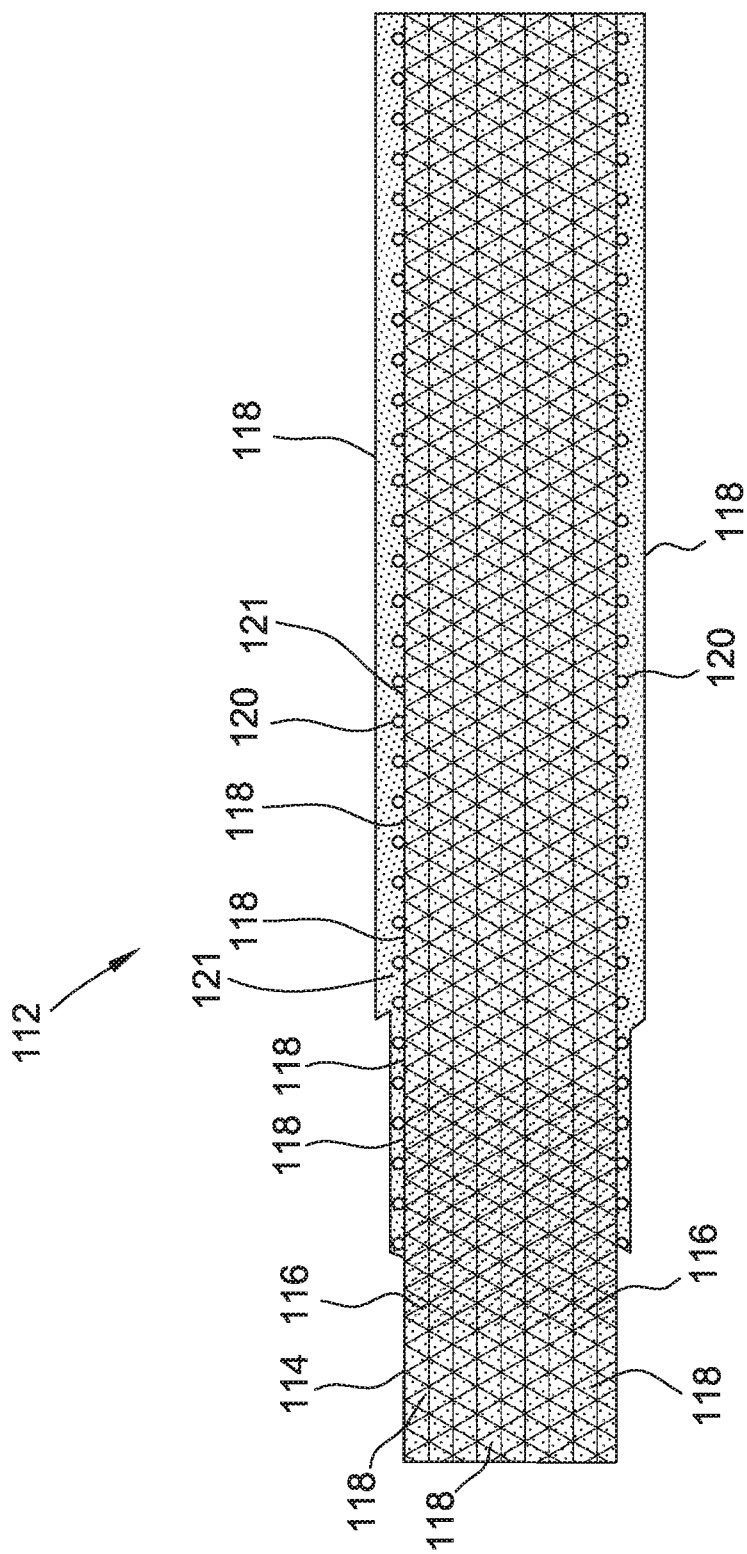
FIG. 5 shows a longitudinal cross-section taken along 5-5 of the medical delivery device of FIG. 4.

Referring now to FIG. 5, there is shown a cross-sectional view of medical delivery device 112 of FIG. 4 taken along line 5-5 to show additional details about the various layers, and specifically the inner surface of device 112. FIG. 5 shows inner layer 114 including thermoplastic elastomer 118 present in plurality of pores 116 of inner layer 114 such that a non-porous composite inner layer including both lubricious material and thermoplastic elastomer is formed. Additionally, FIG. 5 shows metallic layer 120 including thermoplastic elastomer 118 present in plurality of pores 121. As such, the single thermoplastic elastomer present in this embodiment of the medical delivery device intermixes into the plurality of pores of both the lubricious inner layer and the metallic layer.

In a further alternative embodiment of the present disclosure, the medical delivery device includes a structure formed from at least one metallic substrate coated with a lubricous material. Once the metallic substrate(s) has been coated with the lubricious material, the metallic substrate(s) is braided or wound into a coil thus forming a structure comprising a plurality of pores. The structure is then subjected to a reflow (or similar) process with a thermoplastic elastomer over a mandrel, or similar device, as discussed in more detail below. In this embodiment, the lubricious material itself does not contain a plurality of pores as discussed above as the porous nature of the device is created by the braiding, coiling, etc. of the coated substrate material as set forth below.

Figure 6:
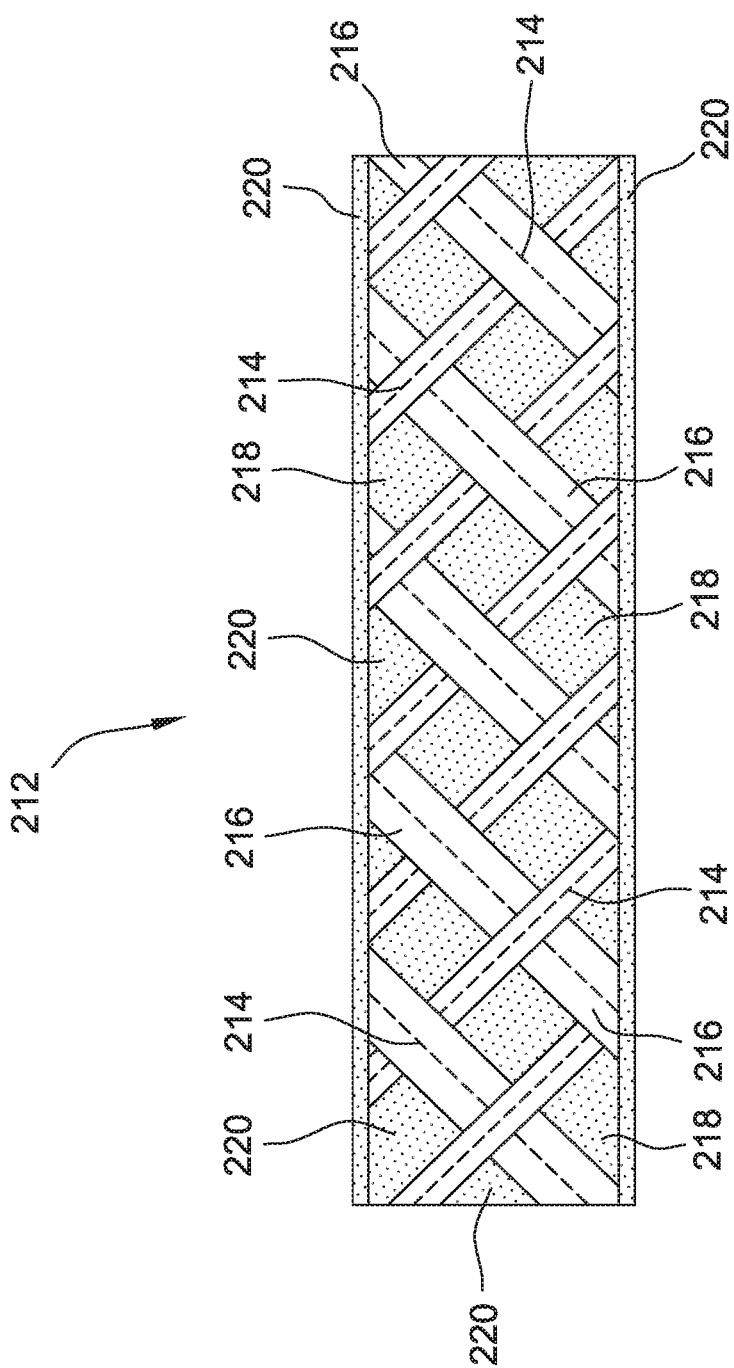
FIG. 6 shows a longitudinal cross-section of another embodiment of a medical delivery device of the present disclosure.

Referring now to FIG. 6, there is shown a longitudinal cross-section of this embodiment wherein medical delivery device 212 includes metallic substrate 214 coated with lubricious material 216. Plurality of pores 218 are substantially filled in with thermoplastic elastomer 220 such that a non-porous composite layer is formed that includes both lubricious material and thermoplastic elastomer. This non-porous composite layer includes properties from both the lubricous material (i.e., low friction) and the thermoplastic elastomer (i.e., durability).

In accordance with various embodiments of the present disclosure, the medical delivery devices including the substantially non-porous composite layer as described herein may be manufactured utilizing any number of suitable manufacturing techniques that can produce the desired layer and/or structure. Although many of the manufacturing techniques described herein utilize a conventional mandrel to manufacture the medical delivery device including the lubricous material having a plurality of pores, one skilled in the art based on the disclosure herein will realize that other techniques that may or may not utilize a mandrel may be suitable as well as the mandrel, which is not a critical component in the manufacturing process. In one embodiment, the medical delivery device is manufactured by first introducing the lubricious material having a plurality of pores onto a mandrel. The lubricious material may be in any number of suitable forms as mentioned above so long as it includes a plurality of pores. In one particular embodiment, the lubricious material is tubular having a plurality of pores that is introduced onto the mandrel where a first thermoplastic elastomer is melted and reflowed over it to allow the thermoplastic elastomer to substantially fill in the plurality of pores in a first step. The first reflowed thermoplastic elastomer coats the surface of the lubricious material and flows into the pores thus creating a substantially non-porous composite liner. The outer surface (i.e., the surface facing away from the mandrel) is substantially completely coated with the first thermoplastic elastomer and the inner surface (i.e., the surface facing the mandrel) is a combination of lubricious material and first reflowed thermoplastic elastomer (present in the plurality of pores); that is, the inner surface includes attributes present in both the lubricious material and the reflowed thermoplastic material.

Figure 7:
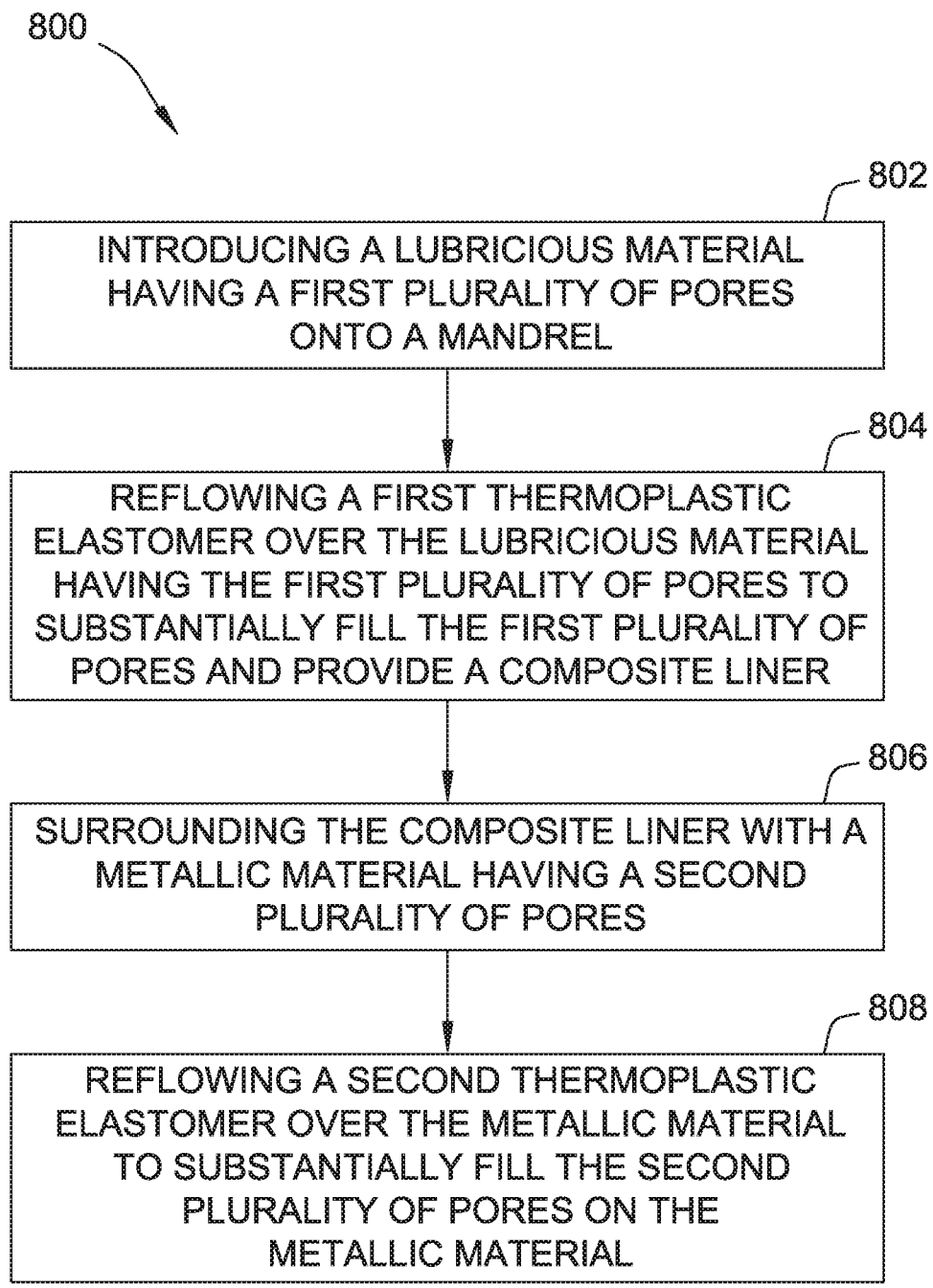
FIG. 7 is a flow chart of one embodiment of a method of making a medical delivery device of the present disclosure.

Once the first thermoplastic elastomer has been reflowed onto the lubricous material to form the non-porous composite liner, the composite liner may be surrounded with a metallic material having a plurality of pores as described above. After the metallic material having a plurality of pores has been placed around the composite liner, a second thermoplastic elastomer (which may be the same or different from the first thermoplastic elastomer) is melted and reflowed over the metallic material to substantially fill the plurality of pores on the metallic material and form the medical delivery device. FIG. 7 is a flow chart that further illustrates this exemplary method. Method 800 includes introducing 802 a lubricious material having a first plurality of pores onto a mandrel; reflowing 804 a first thermoplastic elastomer over the lubricious material having the first plurality of pores to substantially fill the first plurality of pores and provide a composite liner; surrounding 806 the composite liner with a metallic material having a second plurality of pores; and reflowing 808 a second thermoplastic elastomer over the metallic material to substantially fill the second plurality of pores on the metallic material.

Figure 8:
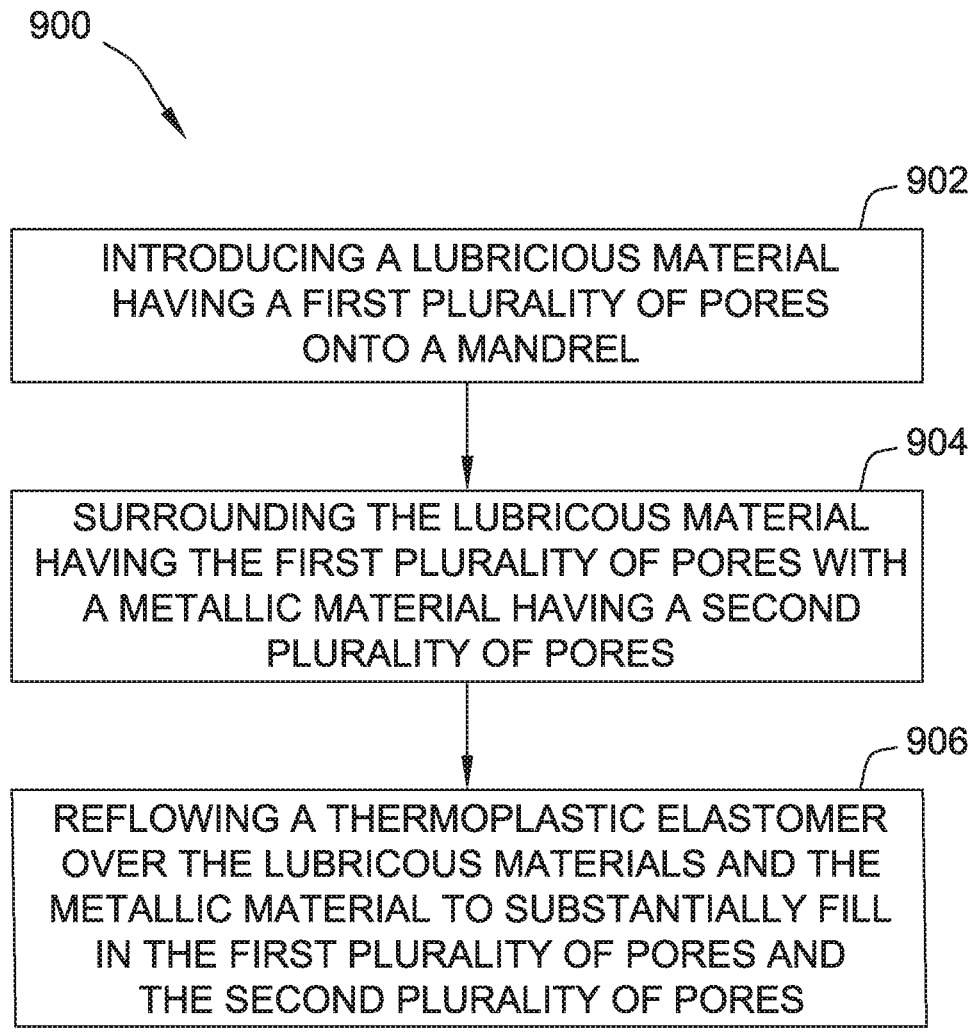
FIG. 8 is a flow chart of another embodiment of a method of making a medical delivery device of the present disclosure.

In another embodiment of the present disclosure, the medical delivery device is manufactured by first introducing a lubricious material having a plurality of pores onto a mandrel and surrounding lubricous material with a metallic material having a plurality of pores. Once the metallic material is in place surrounding the lubricious material, a thermoplastic elastomer is melted and reflowed over the metallic material and lubricious material to substantially fill in the plurality of pores on the lubricious material and the plurality of pores on the metallic material to form the medical delivery device. In this embodiment, only a single reflowing of the thermoplastic elastomer is utilized to simultaneously substantially fill in the plurality of pores present in the lubricous material and in the metallic material. FIG. 8 is a flow chart that further illustrates this exemplary method. Method 900 includes introducing 902 a lubricious material having a first plurality of pores onto a mandrel; surrounding 904 the lubricous material having the first plurality of pores with a metallic material having a second plurality of pores; and reflowing 906 a thermoplastic elastomer over the lubricous material and the metallic material to substantially fill in the first plurality of pores and the second plurality of pores.

In another embodiment of the present disclosure, the medical delivery device is manufactured by first coating a metallic substrate (which, as noted above, could be a single metallic substrate or multiple metallic substrates) with a lubricous material. The metallic substrate may be any suitable metallic material known in the art including, for example, stainless steel, a stainless steel alloy, and the like. In this embodiment, the lubricious material coated onto the metallic substrate may be any of the lubricious materials described above but need not include a plurality of pores as the plurality of pores in this embodiment is created by the processing of the coated metallic substrate as described below.

Once coated with the lubricious material, the coated metallic substrate may then be introduced onto a mandrel or similar device for further processing to create a porous structure. In some embodiments, the coated metallic substrate may be braided on the mandrel to form the desired structure, such as a braided metallic tube or the like. In other embodiments, the coated metallic substrate may be wound like a coil on the mandrel to form the desired structure. Other methods of preparing the coated metallic substrate for further processing are within the scope of the present disclosure as well so long as these methods result in a porous structure; that is, the exact braiding, coiling, or other processing technique is not critical so long as the resulting structure produced includes a plurality of pores therein.

Once the coated metallic substrate has been braided, wound, or otherwise processed, a thermoplastic elastomer is melted and reflowed over the structure including the metallic substrate having the lubricious material coating to substantially fill in the plurality pores (i.e., gaps or openings in the braid, coil, etc.) present and form the medical delivery device. In this embodiment, the inner layer of the structure is a coated metallic substrate that has a composite-type configuration where both the lubricious material and the thermoplastic elastomer are present on the inner surface thereof.

Figure 9:
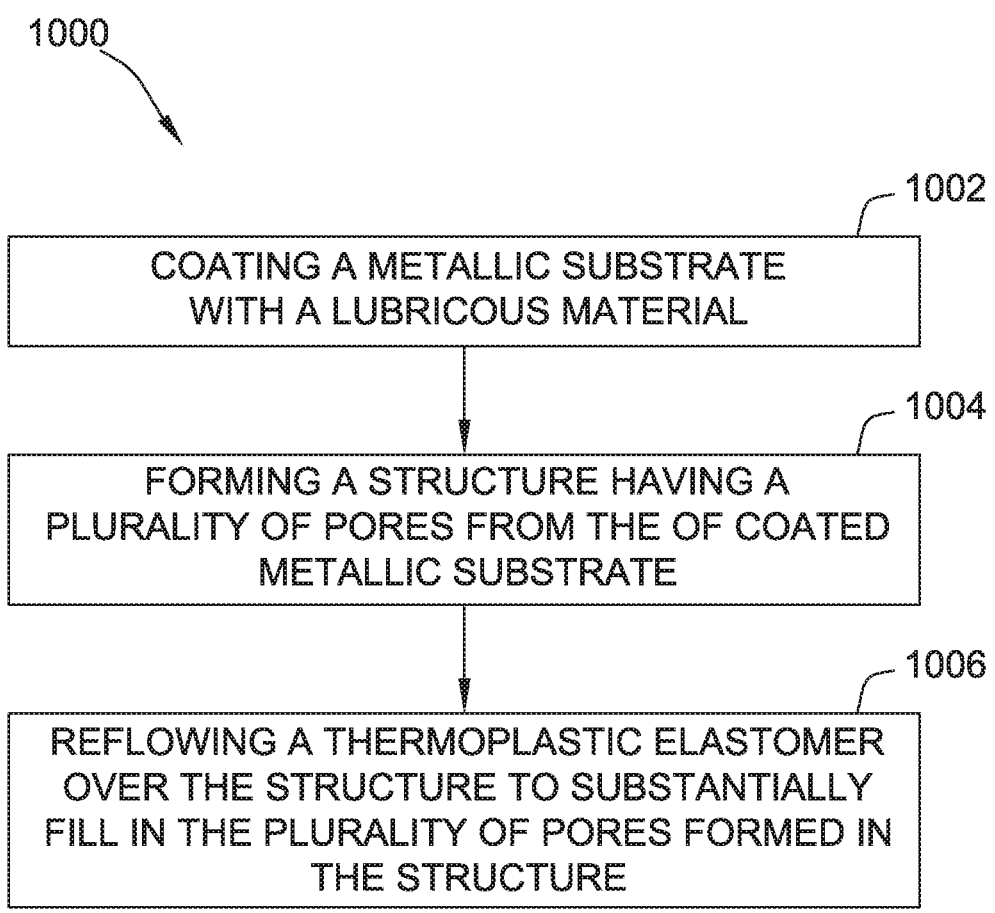
FIG. 9 is a flow chart of another embodiment of a method of making a medical delivery device of the present disclosure.

FIG. 9 is a flow chart that further illustrates this exemplary method. Method 1000 includes coating 1002 a metallic substrate with a lubricous material; forming 1004 a structure having a plurality of pores from the coated metallic substrate; and reflowing 1006 a thermoplastic elastomer over the structure to substantially fill in the plurality of pores formed in the structure.

The medical delivery devices of the present disclosure may be used as a pathway to deliver a multitude of medical devices into a subject, and specifically into the vasculature of a subject. In many embodiments the devices are specifically suitable for introducing a medical device into a heart chamber. Although the medical delivery devices as described herein may be sized and configured in a variety of ways to accommodate a variety of uses, some common sizes for the devices described herein are 9 Fr, 10 Fr, 12 Fr, 13 Fr, and 14 Fr as well as other sizes.

Although a number embodiments of this disclosure have been described above with a certain degree of particularity, those skilled in the art could make numerous alterations to the disclosed embodiments without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

EXAMPLE 1

The following Example illustrates a specific embodiment and/or feature of a medical delivery device that includes a lubricous material having a plurality of pores therein that have been substantially filled with a reflowed thermoplastic elastomer to produce a substantially non-porous composite liner as described herein. The Example is given solely for the purpose of illustration and is not to be construed as a limitation of the present disclosure, as many variations thereof are possible without departing from the spirit and scope of the disclosure.

In this Example, a medical delivery device of the present disclosure was manufactured and its performance in delivering a 34 millimeter left atrial appendage occluder evaluated and compared to the performance of a conventional medical delivery device. The medical delivery device of this Example was manufactured by first braiding a polytetrafluoroethylene (PTFE) monofilament fiber (0.004 inch diameter) (Zeus Inc., Orangeburg, S.C.) on a mandrel (0.189 inch) to provide a lubricious material having a plurality of pores therein. Once the braiding of the PTFE monofilament fiber was complete, 72D PEBAX® (Arkema, Colombes, France) was melted and reflowed over the braided PTFE positioned on the mandrel. After the reflow with the 72D PEBAX was complete, 0.0015 inch stainless steel wire was braided over the PEBAX layer and 63D PEBAX® was melted and reflowed over the braided stainless steel to provide the outer jacket of the medical delivery device.

The medical delivery device of this Example was then loaded with a 34 millimeter left atrial appendage occluder and the occluder advanced through the medical delivery device and deployed. The force required to advance and deploy the occluder with the medical delivery device of this Example was comparable to the force required to advance and deploy the same occluder through a conventional medical delivery device that included an extruded PTFE liner. The force required to recapture the occluder into the medical delivery device of this Example was also comparable to the force required with a conventional medical delivery device. Further, after recapture and re-deployment of the occlude durability was improved as compared to the conventional extruded PTFE liner.

What is claimed is:

1. A medical delivery device comprising:
   a substantially non-porous composite liner as an inner-most layer of the medical delivery device comprising:
      an inner-most layer comprising a lubricious material having a first plurality of pores; and
      a first reflowed thermoplastic elastomer substantially filling the first plurality of pores;
   a metallic material having a second plurality of pores surrounding an entire length of the substantially non-porous composite liner; and
   a second reflowed thermoplastic elastomer substantially filling the second plurality of pores in the metallic material.

2. The medical delivery device of claim 1, wherein the lubricious material is selected from the group consisting of polytetrafluoroethylene, fluorinated ethylene propylene, polyethylene terephthalate, and combinations thereof.

3. The medical delivery device of claim 1, wherein the lubricious material is in a form selected from the group consisting of a mesh, a braid, and a wound coil.

4. The medical delivery device of claim 1, wherein the first reflowed thermoplastic elastomer is selected from the group consisting of a polystyrene, polyvinyl chloride, ethylene vinyl acetate, polyether block amide, a polyamide, a thermoplastic polyurethane, and combinations thereof.

* * * * *